(12) United States Patent
Stockert et al.

(10) Patent No.: US 11,829,511 B2
(45) Date of Patent: Nov. 28, 2023

(54) MEDICAL DATA ACCESS RIGHTS CONSTRAINT ENFORCEMENT AND PRESENTATION SYSTEM

(71) Applicant: Health2047, Inc., Menlo Park, CA (US)

(72) Inventors: Jack Stockert, Los Altos, CA (US); Charles Aunger, Hayward, CA (US); Karl Ronn, Palo Alto, CA (US)

(73) Assignee: Health2047, Inc., Menlo Park, CA (US)

( * ) Notice: Subject to any disclaimer, the term of this patent is extended or adjusted under 35 U.S.C. 154(b) by 0 days.

(21) Appl. No.: 17/644,924

(22) Filed: Dec. 17, 2021

(65) Prior Publication Data
US 2022/0253552 A1 Aug. 11, 2022

Related U.S. Application Data

(63) Continuation of application No. 16/522,520, filed on Jul. 25, 2019, now Pat. No. 11,210,418.

(60) Provisional application No. 62/703,645, filed on Jul. 26, 2018.

(51) Int. Cl.
*G06F 21/62* (2013.01)
*G06F 9/451* (2018.01)
*G16H 10/60* (2018.01)
*G16H 40/67* (2018.01)

(52) U.S. Cl.
CPC .......... *G06F 21/6245* (2013.01); *G06F 9/451* (2018.02); *G16H 10/60* (2018.01); *G16H 40/67* (2018.01)

(58) Field of Classification Search
CPC ..... G06F 21/6245; G06F 9/451; G16H 10/60; G16H 40/67
See application file for complete search history.

(56) References Cited

U.S. PATENT DOCUMENTS

2018/0150650 A1* 5/2018 Saunders .............. H04L 63/104

OTHER PUBLICATIONS

Li et al. "Securing personal health records in cloud computing: Patient-centric and fine-grained data access control in multi-owner settings," International conference on security and privacy in communication systems, Springer, Berlin, Heidelberg, 2010 Available at—https://rdcu.be/c3x7U.*

Katt et al. "A general obligation model and continuity: enhanced policy enforcement engine for usage control," Proceedings of the 13th ACM symposium on Access control models and technologies, 2008.*

* cited by examiner

*Primary Examiner* — Pei Yong Weng
(74) *Attorney, Agent, or Firm* — Knobbe, Martens, Olson & Bear, LLP

(57) ABSTRACT

Systems and methods for medical data access rights constraint enforcement and presentation. One of the methods includes obtaining a plurality of agreements, the agreements including indications of data access rights to portions of medical data; determining, based on the agreements, data access rights for a plurality of patients, the data access rights constraining access to portions of medical associated with the patients, and the data access rights requiring authorization of one or more entities generating, for at least one patient, a data access table representing a graphical depiction of data access rights of the at least one patient; and causing presentation of the data access table.

20 Claims, 7 Drawing Sheets

Use Case A 210

| Data Right | Hospital | Medical Professional | Patient |
|---|---|---|---|
| Type A | ● | ● | ○ |
| Type B | ● | ● | ● |
| Type C | ● | ● | ● |
| Type D | ○ | ○ | ○ |

Use Case N 212

| Data Right | Hospital | Medical Professional | Patient |
|---|---|---|---|
| Type A | ○ | ○ | ○ |
| Type B | ● | ● | ○ |
| Type C | ● | ● | ● |
| Type D | ● | ○ | ○ |

FIG. 2B

MEDICAL DATA ACCESS RIGHTS CONSTRAINT ENFORCEMENT AND PRESENTATION SYSTEM

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure relates to systems and techniques for security, data integration, and visualization. More specifically, this disclosure relates to establishing data rights to medical data.

BACKGROUND

Medical data may generally be stored in electronic medical record (EMR) systems. Example EMR systems may be located at hospitals. These EMR systems may store medical data for different patients, such that medical professionals may access the medical data to administer medical care. For example, an EMR system may provide a front-end user interface for entry of medical data related to a specific patient. The EMR system may further present previously entered medical data, medical images, and so on. EMR systems may additionally store information generated by medical professionals, such as notes related to administering medical care. Via use of these EMR systems, medical data may be shared between medical professionals. Generally, EMR systems may be proprietary. Thus, sharing of medical data between disparate EMR systems may present technical hurdles. It should be appreciated that medical data may also be restricted in its ability to be shared. For example, the Health Insurance Portability and Accountability Act (HIPAA) may limit scenarios in which medical data may be shared.

Commonly, hospitals may have multitudes of agreements which memorialize information associated with access rights to medical data. These agreements may be consented to by patients, and indicate access rights to the patients' medical data. An example of an access right may include limits associated with sharing medical data. For example, a first agreement may indicate that certain medical data may be shared with an outside party. In this example, the medical data may be required to be anonymized, such as via removal of protected health information (PHI). The outside party may, as an example, represent a research entity. As another example, a second agreement may indicate that certain medical data may be shared upon authorization by a patient. Thus, the patient may be required to affirmatively indicate consent to each instance of sharing. Agreements may additionally be specific to types of diseases or may indicate specific use cases for which medical data can be shared. For example, medical data of a patient which is associated with a type of cancer may be shared with a research entity. In this example, medical data of the patient not associated with the type of cancer may not be shared.

Each hospital, or medical care provider, may have different agreements. A research entity may have difficulty navigating among these agreements to obtain medical data. For example, a research entity may require large quantities of certain types of medical data for use in training machine learning models. However, the researcher may have to negotiate between multitudes of hospitals to obtain sufficient medical data. Each hospital may then have to analyze its unique agreements executed for all patients to determine whether it can share such medical data. These agreements may be difficult to analyze and maintain. For example, sunset provisions may alter data rights at specific dates.

SUMMARY

Particular embodiments of the subject matter described in this specification can be implemented so as to realize one or more of the following advantages. A system described herein can ingest agreements associated with a hospital. The system can then automatically generate a user interface describing medical data access rights authorized by the agreements. As an example, a first agreement may indicate that imaging data may be shared with an outside entity for specific search purposes. In this example, a patient may have executed the first agreement. The generated user interface may therefore graphically depict that both the hospital and the patient have authorized sharing of imaging data. For example, the graphical depiction may include a table identifying different data access rights. The table may further depict whether different entities have consented to sharing each data access right. Example entities may include a hospital, a patient, a medical professional, a researcher, and so on.

In this way, an entity may use the above-described user interface to rapidly identify data access rights which are available for each patient. For example, a hospital may review the user interface to ascertain whether imaging data may be shared with an outside research entity. In this example, sharing of imaging data may be characterized as a data access right. For example, sharing of imaging data may be a type of data access right included in the above-described table. Through the succinct user interfaces described herein, the hospital may thus quickly determine whether such sharing is authorized by one or more patients.

As will be described, the agreements may indicate data access rights which vary based on a type, or portion, of medical data. Example types may include imaging data, notes, patient lab data, and so on. Thus, the user interfaces described herein may indicate data access rights specific to types of medical data. As described above, the user interfaces may, in some embodiments, depict a table identifying data access rights. This table may therefore identify whether the entities described above consented to sharing each type of medical data.

It should be appreciated that one or more types of medical data may require hospital, medical professional, and patient approval to share the medical data with an outside entity. For example, notes authored by a medical professional may require consent of these entities. In this example, the notes may relate to a patient and thus require patient consent to an outside entity accessing the notes. Furthermore, since the medical professional authored the notes the medical professional may be required to consent. Additionally, since the hospital employs the medical professional the hospital may be required to consent. Similarly, one or more other types of medical data may require either only hospital approval or only patient approval. As an example, particular, types of medical data may not include protected health information. For these types of information, the hospital may not require affirmative patient consent. As another example, patient lab data may solely require patient approval.

With respect to the above-described complexities of data access rights, the user interfaces may succinctly present these complexities. Thus, a user of a user interface described herein may quickly ascertain the boundaries of data access rights. In this way, and with respect to the above-described example of notes, any ambiguity about sharing such notes may be removed.

Therefore, the user interfaces described herein improve efficiencies associated with use of user interfaces. Prior user interfaces may enable presentation of the text obtained from selected agreements. For example, a user may navigate a particular application on his/her user device. The user may then search for a specific agreement executed by a patient. The user may then analyze the specific agreement to ascertain data access rights associated with the patient. In this way, the user may determine an extent to which the patient's medical data is authorized to be shared.

However, there may be multitudes of different agreements being used. For example, there may be different versions of an agreement. As another example, there may be different types of agreements in place each with different access rights described therein. Thus, it may present a tremendous technical burden on a hospital to ascertain an extent to which medical data may be shared. As an example, a research entity may request medical data of a certain type from the hospital. In this example, the hospital may be required to identify medical data of the certain type. The hospital may then be required to individually review all agreements signed by patients associated with the identified medical data.

In contrast to the above, the user interface described herein can succinctly present complex information that describes hundreds, thousands, and so on, different agreements. Thus, a user may quickly navigate about the user interface. The user may rapidly ascertain whether the above-described research entity's request may be serviced.

To ensure validity of data access rights determined from ingesting executed agreements, the system may use machine learning models. These models may optionally be trained to implement natural language processing, such as natural language understanding techniques. As an example, the system may receive training data comprising agreements. This training data may be labeled such that portions of the agreements may be understood to correspond to specific data access rights. Example deep-learning techniques, such as recurrent neural network techniques, may be employed to analyze agreements.

Additionally, the system may learn a hospital's preferred format or template for agreements. As will be described below, the system may enable a user to toggle data access rights on or off for specific types of medical data. For example, a user interface may be presented that includes selectable options for the toggles. A hospital may use the user interface to efficiently generate agreements according to these toggled data access rights. The generated agreements may then be executed by patients, medical professionals, and so on. Optionally, the agreement may be generated based on a hospital's preferred format or template. Thus, the system described herein may serve as a front-end to creation of agreements.

In addition to the user interfaces, the system may enforce data access rights determined from analyzing multitudes of agreements. For example, the system may receive requests from outside entities requesting accesses to medical data. The system may analyze the requests, and then authorize or deny the requests based on the determined data access rights. The system may therefore advantageously serve as a front-end to a hospital's electronic medical record (EMR) systems. For example, the system may authorize access to the EMR systems. As will be described, the system described herein may be platform agnostic with respect to the EMR systems. As an example, the system may route authorized requests to the EMR systems for processing. The system may further be implemented as a front-end to an EMR system, plug-in to an EMR system, and so on.

Thus, the system can approve or deny requests for specific medical information based on the determined data access rights. In this way, a research entity may request medical data of a certain type from one or more hospitals. The system may determine whether the request may be satisfied for each of the hospitals. Additionally, approving or denying a request may depend on a context for which medical data is being requested. For example, a particular hospital may authorize portions of medical data for university research. Alternatively, the particular hospital may not authorize for-profit corporations to use the medical data. Thus, the system may automatically validate requests based on context. Similarly, approving or denying a request may depend on a particular time the request is received. For example, data access rights may have sunset provisions as recited in agreements. The system may ingest any time constraints indicated in the agreements to use when enforcing data access rights.

Accordingly, in various embodiments, large amounts of data are automatically and dynamically calculated interactively in response to user inputs, and the calculated data can be efficiently and compactly presented to a user by the system. Thus, in some embodiments, the user interfaces described herein are more efficient as compared to previous user interfaces in which data is not dynamically updated and compactly and efficiently presented to the user in response to interactive inputs.

Further, as described herein, the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations compris-

BRIEF DESCRIPTION OF THE DRAWINGS

FIG. 2B illustrates example data access tables that vary based on a context associated with the data access tables.

DETAILED DESCRIPTION

Figure 1:
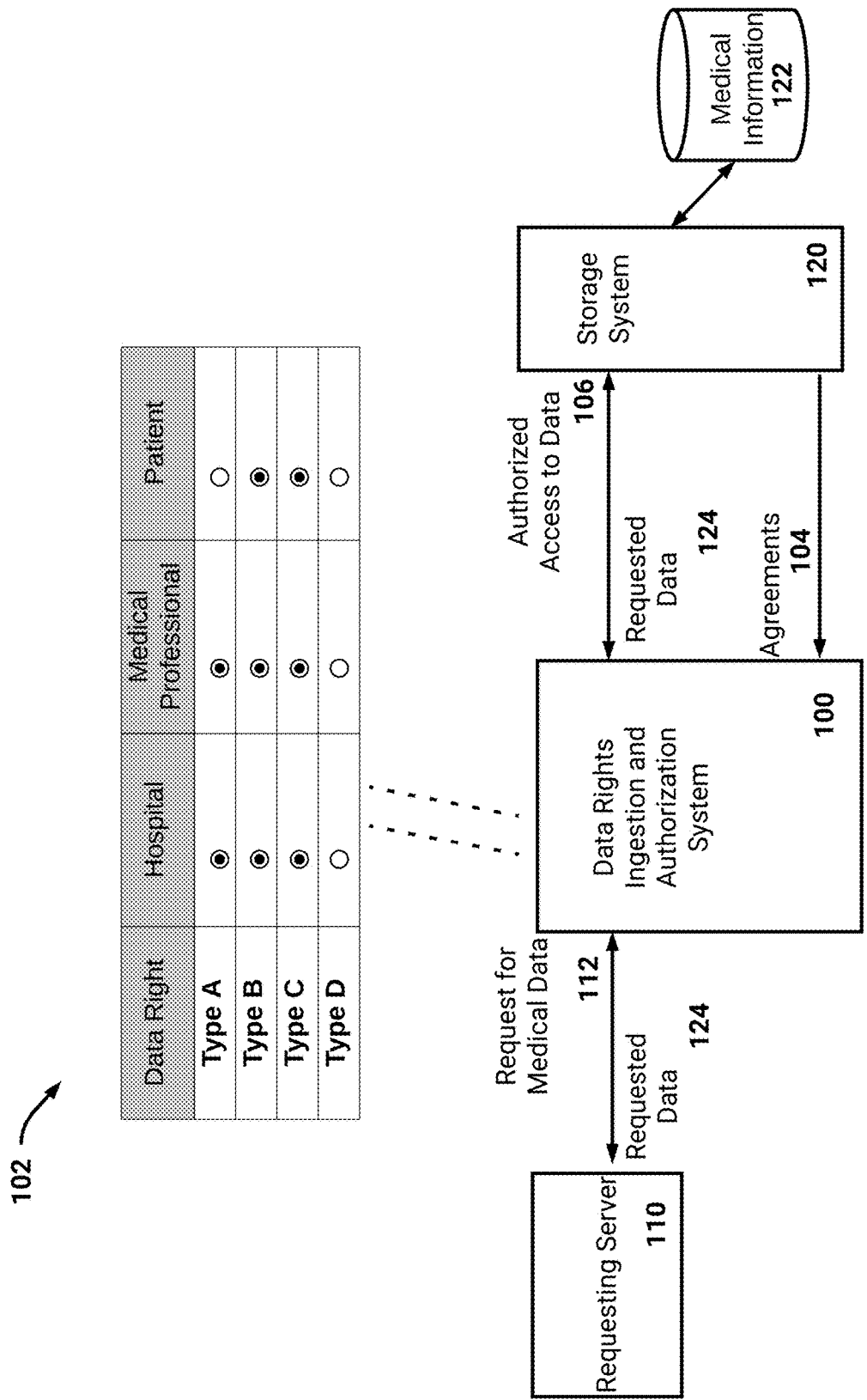
FIG. 1 illustrates an example of a data rights ingestion and authorization system.

This specification describes a system that can analyze agreements describing data access rights to medical data. The agreements may have been executed by patients, medical professionals, hospitals, researchers, and so on. The system can then present user interfaces summarizing different data access rights extracted from the agreements. Advantageously, and as will be described, users of the hospital may provide queries associated with interrogating the analyzed agreements. As an example, a user of the hospital may provide a query to determine whether sharing of anonymized x-ray images is authorized by the hospital's patients. In some embodiments, the system may additionally receive requests for access to medical data. The system may authorize such requests based on the data access rights extracted from the agreements. The system may be, for example, the data rights ingestion and authorization system 100 described below.

It should be appreciated that hospitals may have thousands or more agreements in place with different patients, medical professionals, and/or other entities. Example entities may include entities performing medical research, pharmaceutical companies, and so on. These agreements can memorialize an extent to which medical data may be accessed. An example of access may include sharing of the medical data. However maintaining these agreements may present technological problems. For example, a hospital may use printed agreements which are hand-signed by patients. Thus, the hospital may have to store these agreements in physical files. Additionally, digitized versions of these agreements may be unable to be rapidly analyzed. For example, the hospital may be required to open each digitized agreement on a user device and review it. In this way, the agreements may be unable to be easily interrogated by the hospital to ascertain data access rights summary information for its patients.

As will be described, the system described herein may thus enable a holistic view into analyzed agreements. In this way, a hospital may quickly be presented with summary information associated with any of the hospital's agreements. For example, the summary information may reflect data access rights for a particular patient or for a group of patients. As another example, the summary information may reflect average data access rights of the hospital's patients. As another example, the summary information may reflect data access rights of patients who are outliers. In this example, the hospital may identify patients who have signed agreements which provide for atypical data access rights as compared to other patients of the hospital.

Without the techniques described herein, and as an example, a hospital or other entity may be technically unable to timely respond to requests for medical information. For example, it may be advantageous for a hospital to connect patients with a particular disease to a pharmaceutical company testing a drug to combat the particular disease. However, in this example the hospital would have to identify patients with the particular disease. The hospital would then have to manually review agreements executed by the identified patients. The hospital may then be required to individually contact each patient and indicate that such a drug trial is available.

In contrast, the innovative techniques described herein may address the above-described problem. For example, the system described herein may analyze agreements signed by the above-described hospital's patients. The system may additionally interface with one or more electronic medical record (EMR) systems of the hospital. Thus, the system may identify patients with the particular disease. The system may present information indicating whether the identified patients' consented to sharing of information for drug trials. In some embodiments, the system may notify the identified patients of the drug trial. For example, notifications may be provided as text message, automated phone calls, or as information pushed to an application executing on the patient's user devices. In this way, the hospital may rapidly connect these patients to the pharmaceutical company.

Advantageously, in some embodiments the pharmaceutical company may provide a request to the system. For example, the system may respond to application programming interface (API) calls or endpoints. In this example, the pharmaceutical company may provide a request associated with connecting to patients with the particular disease. As described above, the system may automatically notify patients of the drug trial. A patient may thus affirmatively indicate whether he/she wishes to join the drug trial.

As another example of a request, the pharmaceutical company may request certain types of anonymized medical data of patients who match certain features. These features may be related to symptoms of the particular disease. The pharmaceutical company may use the anonymized medical data to understand the disease or train machine learning models. The system may analyze executed agreements and determine whether this request may be satisfied. The anonymized medical data may enable the pharmaceutical company to identify one or more patients as being a candidate for a pharmaceutical drug trial. Since the medical data is anonymized, the pharmaceutical company may thus provide a request to connect with the patients. In some embodiments, the system may thus notify the patients as described above. In this way, the patients may sign up for a drug trial which may improve the patients' chances of overcoming the particular disease.

As will be described, the system may determine data access rights related to portions of medical data. Example portions of medical data may include types of medical data. To determine the data access rights, the system may parse agreements for indications of data access rights recited therein. Optionally, the system may rely upon machine learning techniques to extract data access rights. For example, word-embedding techniques (e.g., word2vec, deep-learning techniques such as based on word2vec, universal sentence encoder), convolutional neural network techniques, recurrent neural network techniques, and so on, may be used. Optionally, the system may identify particular terms and determine the data access rights based on the particular terms. As an example, an agreement may specify that a patient authorizes a portion of medical data (e.g., imaging data) to be shared with a specific entity. The system may identify the term 'imaging data,' or synonyms thereof, and analyze the text surrounding the term for indications of authorization. Optionally, a user of the system may review an agreement, or a template of an agreement, and specify the data access rights.

Additionally, the determined data access rights may be constrained according to a context in which medical data is used. For example, a hospital may have agreements in place which enable machine learning models to be trained using large sets of specific portions of its stored medical data. Thus, the determined access rights may indicate that the specific portions can be shared for use as training data. The context may optionally be further refined. As an example, the agreements may limit sharing of the medical data for use in homomorphically encrypted machine learning models. Thus, the specific portions may be shared only as homomorphically encrypted information. In this way, an outside entity may train its machine learning models without direct access to unencrypted medical data.

Similarly, the determined data access rights may be constrained according to time. For example, a patient may authorize his/her lab data to be sharable with entities for a specific period of time. An agreement executed by the patient may therefore specify this period of time. The system can analyze the agreement and extract the relevant time component. A user interface describing data access rights associated with the patient may further indicate any constraints as to time.

Thus, the system can generate user interfaces describing data access rights associated with any patient's medical data. A dashboard, for example, may be presented that summarizes authorized data access rights for a patient or a multitude of patients. As described above, specific portions of medical data may be shareable based on authorization by differing types of entities. For example, lab data may be shareable upon authorization by a patient. In contrast, medical notes may be shareable based on authorization by a hospital and a patient. In some jurisdictions, sharing medical notes may also require authorization by a medical professional who authored the medical notes.

Prior to the system ingesting and analyzing agreements from a hospital, the system may turn-off data access rights for the hospital's medical data. As will be described, the system may optionally authorize requests for medical data based on determined access rights. Thus, the system may ensure that requests are denied until the data access rights are determined. The system may also present a dashboard indicating that no data access rights are authorized. For example, a user of the dashboard (e.g., an employee of the hospital) may deny requests for medical information until the data access rights are determined by the system.

Subsequent to analyzing agreements, the dashboard may reflect the data access rights determined from the agreements. For example, the dashboard may enable a user to specify a particular patient. The user may then be presented with a graphical representation of the determined data access rights for the patient. The graphical representation may be referred to herein as a data access table. An example data access table 102 is illustrated in FIG. 1. As another example, the dashboard may enable a user to provide a generalized query. The system may respond to the query based on the determined data access rights. In this example, a query may be a request to identify specific patients who satisfy specific features. The query may further limit the request to only those patients whose medical data may be shared. The query may further limit the request to only those patients whose medical data may be shared with a specific entity or type of entity. In response to the query, the system may determine information satisfying constraints indicated in the query. In the above-described example, the system may present information identifying the specific patients who satisfy the constraints.

Optionally, the dashboard for a hospital may be accessible by outside entities, such as research groups, pharmaceutical companies, and so on. For example, the dashboard may indicate summary information associated with the hospital's data access rights. Example summary information may indicate an average extent to which each portion of medical data may be shared with an outside entity or specific outside entity. As an example, the summary information may specify that for a particular portion of medical data, greater than a threshold percentage of patients' medical data may be shared. In this way, the outside entity can rapidly ascertain whether the hospital can provide medical data useful to the outside entity.

The system may enable access to specific medical information based on validating data access rights. For example, the system may receive a request from an outside entity for specific portions of medical data. The request may be validated to ensure that the data access rights indicate authorization for the outside entity to access the medical data. The request may then be routed to specific EMRs storing the medical data. The request may also be routed to specific databases or storage systems storing the medical data. Thus, the system may, as an example, function as a data clearinghouse.

The system may therefore optionally interface with multitudes of outside entities. The system may also authorize certain requests while denying other requests. In this way, the system may enable a platform from which medical data can be provided. Since any provided medical data can be assured to have been authorized by any required entity, the platform may serve as a standard scheme to access medical data. The technical scheme described herein can be flexible with respect to a standard, or protocol, that causes transmission of the medical data. In embodiments in which the system functions as a data clearinghouse, the system may authorize requests. These requests may be routed according to a protocol or standard of preference. Therefore, the system may optionally solely validate whether medical data may be provided in response to a request. Upon a successful validation, the system may authorize the request (e.g., sign the request). The system may then leave it to a system storing the medical data to respond (e.g., via a preferred protocol).

A user of the system may view an interactive user interface describing the system authorizing requests for medical data. The user may, as an example, be associated with a particular hospital. The user interface may thus identify summary information associated with requests for medical data stored by, or otherwise associated with, the hospital. Optionally, the user interface may present real-time (e.g., substantially real-time) requests for medical information. For a request, the system may indicate an outside entity requesting the medical data. The system may also indicate portions of medical information being requested. The system may also indicate whether the request is to be authorized based on data access rights determined from the hospital's agreements. The user interface may additionally present an animation illustrating requests being received in real-time or requests received in a selectable time period. In this way, the user may monitor the system's determinations regarding data access rights.

Optionally, the user may select (e.g., via a user interface) a request from an outside entity which was authorized by the system. The system may present the determined access rights related to the patients whose medical data was provided to the outside entity. The user may further select within the user interface to cause presentation of specific portions of agreements. The user may thus ensure that the portions authorize the medical data to be provided. The user may further ensure that any entities required to authorize providing the medical data executed the agreements.

In all situations in which medical data is authorized for access by an outside entity, the medical data may optionally be assured to have protected health information removed. Example protected health information (PHI) may include the PHI identifiers described in HIPAA. As an example, at least 18 identifiers may be removed (e.g., names, geographical identifiers, dates, phone numbers, email addresses, medical record numbers, full face photographic images, biometric identifiers, and so on).

FIG. 1 illustrates an example of a data rights ingestion and authorization system 100. As illustrated, the data rights ingestion and authorization system 100 is illustrated as obtaining agreements 104 and determining a data access table 102. The data access table 102 can summarize data access rights extracted from the agreements 104. For example, the data access table 102 illustrated in FIG. 1 may identify data access rights for a particular patient. As another example, the table 102 may identify data access rights for a group of patients.

The data rights ingestion and authorization system 100 may be a system of one or more computers, a system of one or more virtual machines executing on a system of one or more computers, and so on. In some embodiments, the system 100 may be a cloud service or system which interfaces with systems local to medical care providers. Optionally, the data rights ingestion and authorization system 100 may be a part of a computer system local to a particular medical care provider. For example, the data rights ingestion and authorization system 100 may be included in a particular hospital. Optionally, the data rights ingestion and authorization system 100 may represent software executing on a computer system associated with a medical care provider. The software may be, for example, an application obtained from an electronic application store. Optionally, and as illustrated, the data rights ingestion and authorization system 100 may be in communication with a storage subsystem 120. For example, the storage subsystem 120 may store medical information in one or more databases 122. As will be described, the system 100 may authorize requests 102 for information. The system 100 may then route requested information 124 to one or more requesting servers 110.

As illustrated, the data rights ingestion and authorization system 100 has obtained agreements 104 and determined a data access table 102. The agreements 104 are illustrated as being stored by a storage system (e.g., associated with a hospital). However, it should be understood that the agreements 104 may be provided as an upload to the system 100. For example, certain hospitals may maintain paper copies of agreements 104, rendering them difficult to analyze. The system 100 may obtain digitized versions of these agreements 104. Optionally, the system 100 may obtain images of the agreements 104 as captured by a camera of a user device. The system 100 may optionally provide the agreements 104 to an outside system to obtain the included text. The system 100 may also perform an optical character recognition process.

The data rights ingestion and authorization system 100 may extract, or determine, data access rights specified in the agreements 104. As an example, the system 100 may group all agreements related to a specific patient. Certain electronic medical record (EMR) systems may enable access to such agreements via an application programming interface (API) call or endpoint to the EMR systems. For example, the API call can specify a particular patient and request any agreements executed by the patient. Optionally, the agreements may be obtained via a database call, via an operating system search, and so on. For example, the data rights ingestion and authorization system 100 may obtain an indication of all patients. The system 100 may then traverse through the patients. For each patient, the system 100 may obtain agreements that reference the patient or that result from a database or operating system search. While the description above referenced agreements that were executed by a patient, it should be understood that an agreement may relate to a patient without being executed by the patient. For example, a medical professional may have executed agreements with a hospital. These agreements may describe whether the medical professional authorizes data access rights to portions of medical data. While these agreements may not include reference to a patient, they may describe the medical professional's authorization to sharing of medical data associated with patients.

Subsequent to grouping the agreements associated with each patient, the data rights ingestion and authorization system 100 may determine data access rights. As an example, the system 100 may implement one or more machine learning models configured to analyze the agreements. For example, the system 100 may obtain templates of agreements used by hospitals or other medical care providers. Portions of the templates may be labeled, with the labels indicating data access rights being described in the portions. The data rights ingestion and authorization system 100 may then compare the obtained agreements 104 to the templates.

As an example, the agreements 104 may be associated with a specific hospital. The data rights ingestion and authorization system 100 can compare the agreements 104 to one or more templates used by the specific hospital. The templates may optionally vary according to time. For example, the hospital may have multiple versions of the agreement. Thus, the system 100 may advantageously use a template version associated with a same time as an agreement being analyzed. To compare a template with an agreement, the system 100 may determine differences between the two. For example, the agreement may have a patient's name filled in along with address information and so on. The system 100 can analyze the agreement to determine which data access rights portions from the template are included in the agreement. As an example, the system may identify language from the template which is included in the agreement. Optionally, one or more portions of the agreement may be crossed out or lined through in an executed agreement, and the system 100 may indicate that these portions do not authorize data access rights.

As another example, the data rights ingestion and authorization system 100 may use natural language processing techniques to analyze the agreements. For example, the system 100 may parse portions of an agreement (e.g., a contiguous portion). Via the parsing, the system 100 may generate a parse tree. Through utilization of semantic rules learned from analyzing prior agreements, the system 100 may identify portions of each agreement that relate to data access rights. Optionally, the data rights ingestion and authorization system 100 may locate terms indicative of data access rights. The system 100 may then analyze text within a threshold distance of each term.

Based on processing the agreements 104, the data rights ingestion and authorization system 100 may determine data access rights for one or more patients. As described above, data access rights may relate to portions of medical data. The portions may therefore represent distinct buckets of data, which may be separately shared based on language included in the agreements. As illustrated in FIG. 1, the data access table 102 includes four types of medical data (e.g., Type A-D). The system may optionally use the same types of medical data when analyzing agreements from different hospitals. For example, data access rights for the illustrated four types of medical data may be determined for all hospitals.

Optionally, the system may use more, or fewer, types than the four illustrated types. As an example, an EMR system associated with a first hospital may automatically separate medical data into a first number of buckets. As another example, a different EMR associated with a second hospital may separate medical data into a second, different, number of buckets. In these examples, the data rights ingestion and authorization system 100 may determine data access rights for each bucket. Thus, the data access table may include a different number of rows than the table 102 in FIG. 1.

Optionally, the system 100 may associate medical data as stored by an EMR system with different access rights. For example, the system 100 may use a data schema used by the EMR system. As an example, the EMR system may store medical imaging data separately from textual data (e.g., notes). The system 100 may determine data access rights based on analyzing agreements. The system 100 may then access the EMR system's schema, and identify medical imaging data. In this way, the system 100 may learn to associate specific data access rights with portions of stored medical data by an EMR system.

Furthermore, a hospital's agreements may further refine the above-described imaging data. For example, the agreements may indicate separate data access rights to x-ray images as compared to computed tomography images. Thus, the agreements may indicate different data access rights depending on a type of the imaging data. The system 100 may advantageously analyze the EMR system's imaging data and associate the agreements' more detailed data access rights. For example, the system 100 may obtain DICOM imaging data for the stored images. The system 100 may therefore associate data access rights associated with x-ray images to the stored x-ray images. In this way, the system 100 may respond to requests 112 for medical information as described below. For example, a request may relate to x-ray images and the system 100 may therefore obtain the stored x-ray images. In some embodiments, the system 100 may route a request to the EMR system. In these embodiments, the EMR system may obtain the x-ray images.

The data access table 102 illustrates the four data Types A-D, and indicates the entities who have authorized access to the data Types A-D. With respect to Type A, the data access table 102 specifies that a hospital and a medical professional authorize sharing of this medical data. As an example, Type A may relate to cancer diagnoses. This type of data may not require patient approval to share with outside entities. For example, this information may not include protected health information. In contrast, Type B specifies that a hospital, medical professional, and patient have authorized sharing this medical data. This type of data may, as an example, enable an outside entity to identify potential matches to pharmaceutical drug trials. Type D specifies that no entity has authorized sharing this medical data. As an example, Type D may be associated with genomic data. With respect to genomic data, the agreements 104 may not indicate whether genomic data can be shared. Thus, the data rights ingestion and authorization system 100 may identify that this this type of data cannot be shared absent affirmative consent by any required entities.

The data rights ingestion and authorization system 100 may optionally utilize any rules that control whether medical data can be shared. For example, the rules may be associated with legal principles. These rules may thus override data access rights extracted from agreements 104. As an example, a rule may indicate that data Type C cannot be shared even with consent of the entities identified in the data access table 102. Furthermore, particular rules may vary according to location (e.g., state, country). As another example, particular rules may have varying interpretations or may not be clear. In this example, it may be unclear whether medical notes prepared by a medical professional may be shared without consent by the medical professional. Copyright law may, as an example, apply to the medical notes, such that the medical professional is required to indicate consent. However, this may be a grey area based on a current state of the law and/or jurisdiction. Thus, the data rights ingestion and authorization system 100 may advantageously require consent of the medical professional.

Agreements may conflict as to data access rights for a particular patient. For example, a first agreement may indicate that the patient authorized medical image data to be shared. However, a second agreement may indicate that the patient revoked this authorization. Alternatively, the second agreement may indicate that the patient does not consent to medical image data being shared. Advantageously, the data rights ingestion and authorization system 100 can indicate that the patient does not consent to sharing this data. Thus, the data access table 102 may take a conservative view to ensure that data access rights are tightly safeguarded. Optionally, if two agreements conflict the system 100 may identify, or otherwise flag, the two agreements for later review (e.g., by a user). Additionally, the system 100 may present portions of the agreements which conflict to a user for review.

Thus, the data access table 102 may represent a current state of data access rights with respect to medical data stored by the storage system 120. A user may use the data access table 102 to quickly ascertain whether particular medical information may be shared. For example, the table 102 may indicate whether the particular medical information may be shared with an outside entity.

In addition, the agreements 104 may include existing agreements in place with outside entities. The data rights ingestion and authorization system 100 may validate that the data access table 102 supports the existing agreements. For example, an agreement may indicate that an outside entity may use particular medical data to train machine learning models. However, the system 100 may determine that not all patients whose medical data is being used have consented to the use. For example, a first portion of the patients may have signed a different agreement than a second portion. A user may thus cause generation of an agreement for the remaining patients to execute. As an example, the system 100 may use a particular template to automatically generate the agreement.

Optionally, the data rights ingestion and authorization system 100 may respond to requests for medical data 112. As illustrated in FIG. 1, a requesting server 110 may provide a request 112 to the system 100 for handling. The request 112 may optionally be provided over a network (e.g., the internet) and conform to one or more application programming interface (API) calls. The data rights ingestion and authorization system 100 may therefore establish schemes to provide requests for specific medical data. The data rights ingestion and authorization system 100 may then determine whether the request 112 is to be satisfied. For example, the system 100 may use one or data access tables to validate that data access rights are in place such that the request 112 can be satisfied.

The data rights ingestion and authorization system 100 may serve as a front-end to medical data stored at different locations. For example, the system 100 may obtain medical data from different hospitals, research universities, non-profits, governmental entities, and so on. The medical data may be determined to be authorized for access by a requesting server. In this way, the data rights ingestion and authorization system 100 may enable 'single sign on' to different servers or databases storing medical data. It should be appreciated that single sign on can enable a same user account to access different servers. As an example, the Security Assertion Markup Language (SAML) may be employed to achieve single sign on. In this example, different requesting entities may be associated with distinct user accounts configured to access the system 100. The data rights ingestion and authorization system 100 may represent an identity provider which can authenticate entities. For example, the requesting server 110 may provide a user name and password to the system 100 for authentication. The system 100 may then validate that the requesting server 110 is authorized to communicate with systems storing medical data. Based on this validation, the system 100 may determine whether the request 112 can be satisfied. Upon a positive determination, the system 100 may route the request 112 to the storage system 120. The routed request 112 may be adjusted to indicate that the request is authorized to access medical data 106. For example, the system 100 may sign the request 112. As another example, the system 100 may indicate the authorization in a SAML message.

As illustrated, the system 100 has determined that the request 112 can be satisfied. For example, the request may specify types of medical information along with features of patients. An example type of medical information may include medical images. Example features may include particular genomic mutations. Optionally, the request 112 may specify a particular hospital or medical care provider at which the medical data is stored. The system 100 may access data access tables determined for this hospital or medical care provider. If the data access tables support routing this request to the hospital, the system 100 may provide authorized access for data 106 information to storage system 120.

Optionally, the authorized access to data 106 may indicate identifiers (e.g., anonymized identifiers) that are associated with specific patients whose data access tables indicate authorization to the request 112. Optionally, the data 106 may indicate identifiers associated with portions of medical data which are authorized to be provided to the requesting server 110. As an example, an EMR system, or other storage system, may store portions of medical data as being associated with unique identifiers (e.g., cryptographic hashes). The data access tables may be associated with these unique identifiers. Thus, and as an example, Type B medical data in the data access table 102 may be located via the storage system 120. In this way, the data rights ingestion and authorization system 100 may indicate which medical data can be routed to the requesting server 110 while preserving anonymity. In the example of FIG. 1, the data rights ingestion and authorization system 100 has determined that the request 112 can be satisfied. Thus, the system 100 has routed the requested data 124 to the requesting server 110. Optionally, an OAuth token may be used to confirm that the requesting server 110 has successfully been validated and is authorized to obtain the requested data 124.

An example of the data rights ingestion and authorization system 100 servicing an example request follows. A pharmaceutical entity may provide a request 112 to discover patients who may match a set of criteria related to a pharmaceutical being tested. For example, the patients may have multiple myeloma. The system 100 may receive the request 100 and identify whether patients associated with a particular hospital consented to such detection. As described above, the data access tables may indicate that a type of medical data may be related to drug trials. For this example type of medical data, the patient's authorization may be required. Thus, the system 100 may identify one or more patients who have agreed to being discovered for drug trials.

In implementations in which the system 100 acts as a front-end to storage systems, the system 100 may route the above-described request 112 to storage system 120. The request 112 may indicate information identifying the patients. For example, the information may be a unique identifier associated with each patient. In this example, the data access tables for each patient may also be associated with a same unique identifier. In implementations in which the system 100 is located at the hospital, the system 100 may optionally directly cause identification of the patients. Optionally, the system 100 may provide a response to the pharmaceutical entity identifying patients which may be contacted for drug testing. Optionally, the system 100 may activate particular applications executing on user devices of the patients. These particular applications may relay information to the pharmaceutical entity indicating that they are associated with the identified patients. Thus, the system 100 may optionally obfuscate an identity associated with the patients. The patients may use the applications to indicate whether they prefer joining the drug trial.

Figure 2A:
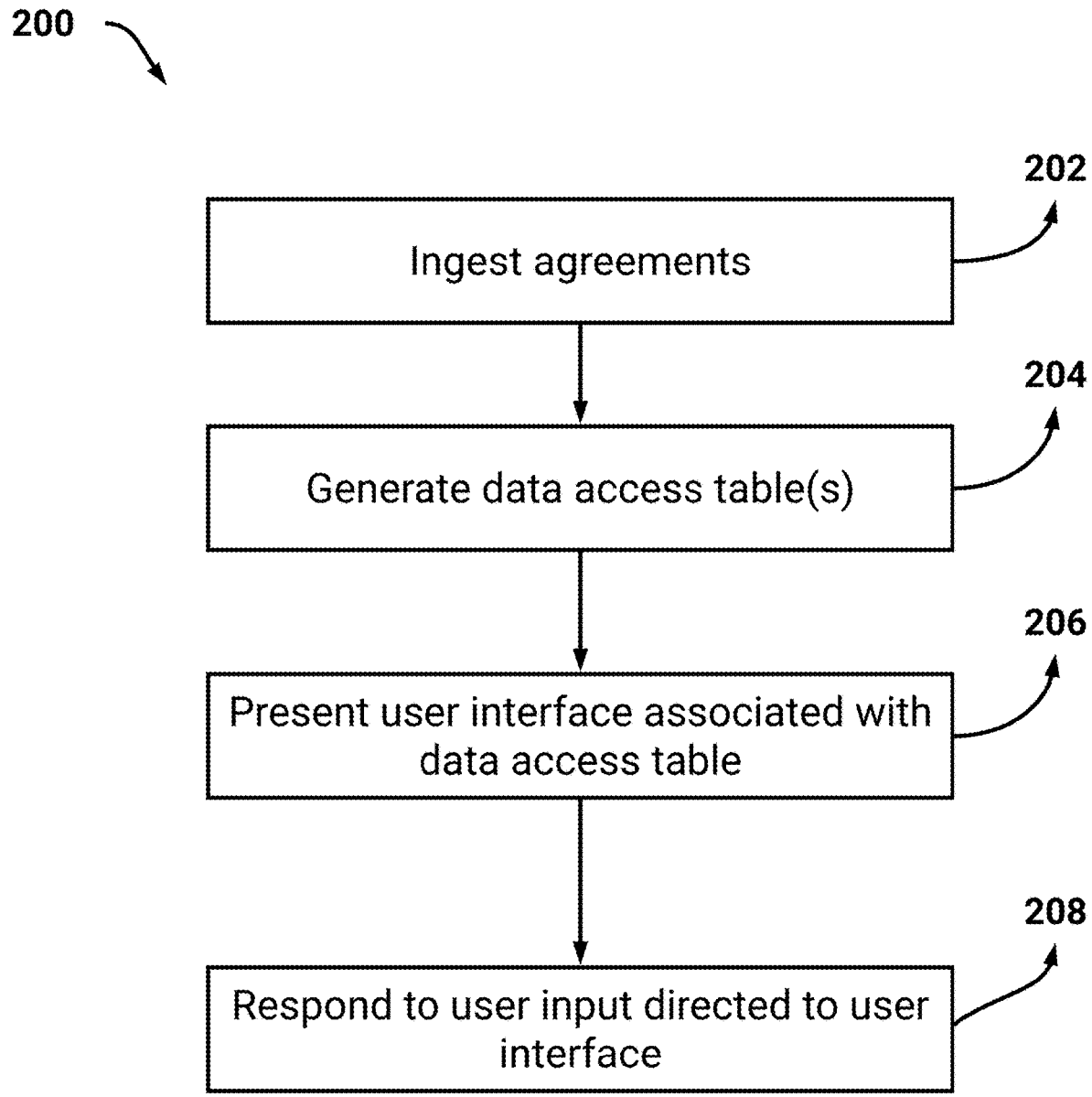
FIG. 2A illustrates a flowchart of an example process for presenting data access rights.

FIG. 2A illustrates a flowchart of an example process 200 for presenting data access rights. For convenience, the process 200 will be described as being performed a system of one or more computers (e.g., the data rights ingestion and authorization system 100).

At block 202, the system ingests agreements. As described above, a hospital may have agreements in place between itself and one or more entities. Example entities may include a patient, a medical professional, an outside entity, and so on. These agreements may specify particular data access rights to portions of medical information. Example portions are described above, and for example presented in FIG. 1 with respect to the data access table 102.

At block 204, the system generates data access tables. A data access table may optionally represent a toggle for each portion of medical data and whether the toggle is on or off for an entity. Each portion of medical data may optionally require particular entities to authorize sharing of the portion. Thus, the data access table may specify whether required entities have toggled data access rights on for each portion of medical information. As illustrated in FIG. 1, the data access table indicates whether different entities have authorized sharing of each type of medical data. The data access table can therefore represent a switchboard identifying whether specific medical data can be shared.

Each patient may have a unique data access table. For example, the system may aggregate agreements related to each patient and may determine (e.g., extract) data access rights from the agreements. Optionally, each patient may have multiple data access tables which vary based on context. Optionally, a same data access table may be associated with contextual access rights. Contexts may relate to a reason for which medical data is to be shared.

FIG. 2B illustrates example data access tables that vary based on a context associated with the data access tables. As illustrated, a first data access table 210 is associated with a first context. An example context may include utilizing medical data for non-profit research. Another example context may relate to for-profit research. Another example context may relate to sharing of contact information (e.g., user names, anonymized contact information, phone numbers) between patients. In this way, the patients may help establish a support group for particular ailments. Another example context may relate receiving information identifying drug trials that may be of benefit to a patient. The system may optionally obtain information identifying pre-defined contexts, and may determine whether the agreements implicate any of the pre-defined contexts.

A second data access table 212 is further illustrated in FIG. 2B. This second data access table 212 may thus relate to a different context than the first data access table 210. As illustrated, Type B data is not authorized by any entity in the second data access table 212. In contrast, Type A data is authorized by a hospital and medical professional entity in the first access table 210.

In the illustrated example, the different contexts are illustrated as being associated with different data access tables. However, it may be appreciated that the different contexts may be identified in a same table. For example, information associated with a same patient may be joined into a same table. Additionally, the description herein describes use of data access tables. However, it may be appreciated that data access rights information may be stored in different data structures or forms. For example, JavaScript object notation (JSON) may be used to represent the data access rights information described herein.

At block 206, the system presents user interface information associated with data access tables. As described in FIG. 1, an example user interface may present a graphical representation of a data access table. For example, table 210 may be presented in an interactive user interface on a user device, such that a user may graphically view data access rights. Optionally, summary information may be generated from the determined data access tables. The summary information may then be presented in the user interface. Example summary information may indicate statistics related to whether each portion of medical information can be shared. For example, summary information may indicate a percentage of patients whose medical data of a particular type can be shared with outside entities.

At block 208, the system responds to user input directed to the user interface. The system may receive user input from a user device of a user viewing the user interface. Optionally, the user interface may be a front-end to a web application executing on the system. The user input may include mouse clicks or keyboard entry of information. Additionally, the user device may include a touch-sensitive display. Thus, portions of the user interface may respond to a user selecting a particular user interface element via touch.

As described above, the system may enable entry of queries via user input. The queries may be analyzed, and the user interface updated to reflect responses. For example, the system may analyze a query in view of the determined data access tables. As an example, a query may request an extent to which a particular type of medical data may be shared. As another example, the query may further indicate a context for which the medical data is to be used. As another example, the query may further indicate a particular outside entity or type of outside entity that is use the medical data. The system may parse this query. The system may then determine whether the data access tables support sharing medical data as identified in the parsed query.

Figure 3A:
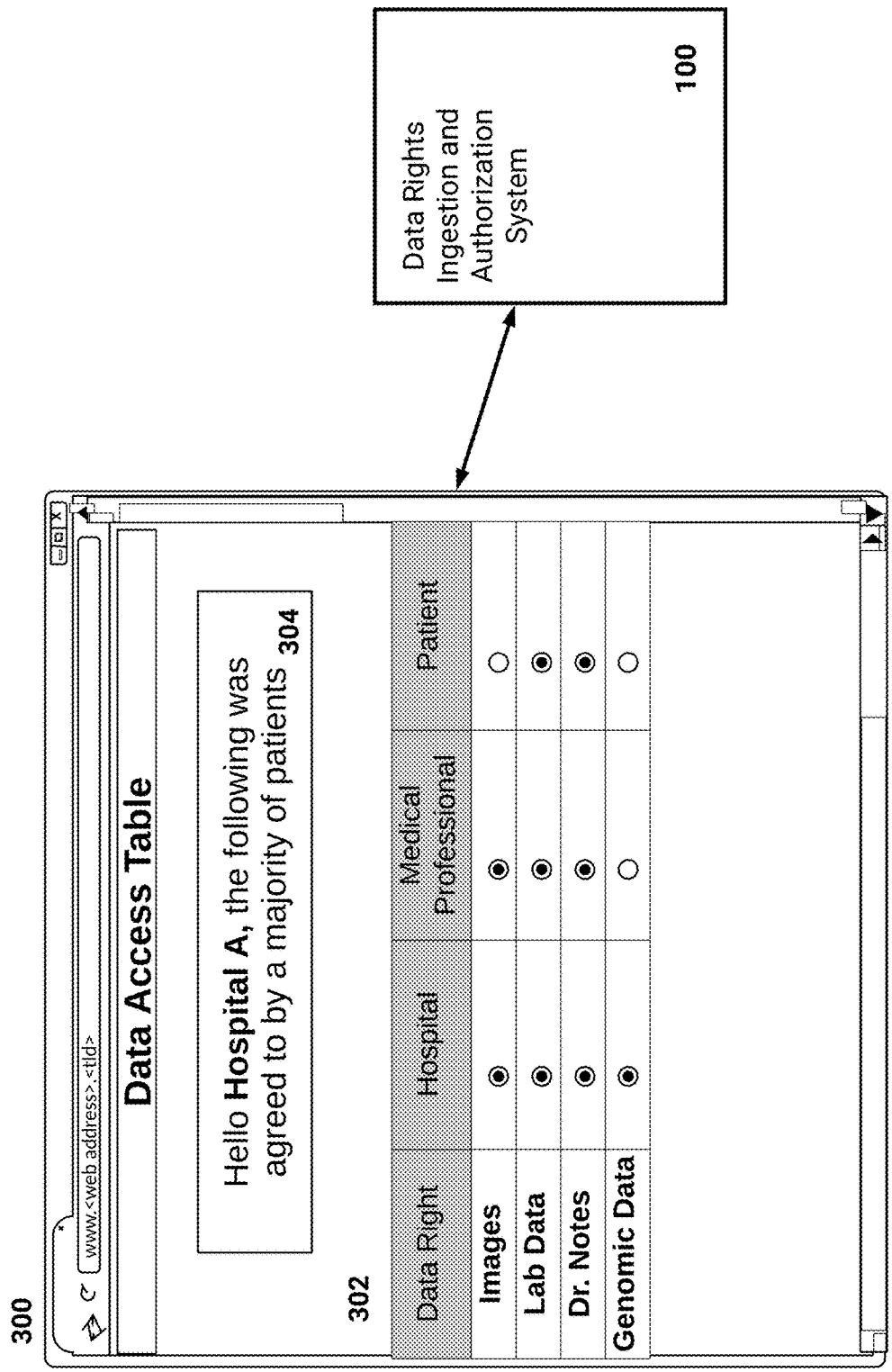
FIG. 3A illustrates an example user interface presenting a data access table on a user device.

FIG. 3A illustrates an example user interface 300 presenting a data access table on a user device. As described in FIG. 2A, a system may generate data access tables for presentation on user devices of users. In this way, a hospital or other medical care provider may view succinct information describing the data access rights included in their agreements. The user interface 300 of FIG. 3A may therefore be generated by the system for presentation on the user device. Optionally, the user device may execute an application (e.g., an 'app' obtained from an electronic application store) that receives information from the system. For example, the application may generate, at least in part, a user interface for presentation on the user device. The application may then receive information from the system sufficient to generate data access tables. Example received information may indicate, for example in a JSON request, the entities who authorized access to each portion of medical data represented in a data access table.

As illustrated, a data access table 302 is included in user interface 300. The data access table specifies entities who have authorized sharing of specific types of medical data. Authorization for these specified entities may be represented as toggles, or other user interface elements. Example user interface elements may include check marks, buttons, and so on. For example, image data is indicated as being authorized by a hospital and a medical professional. As another example, lab data is indicated as being authorized by the hospital, medical professional, and patient. It should be appreciated that different types of medical information may be shared with less than all of the entities listed. For example, lab data may be shared via consent of the patient alone. Thus, optionally the data access table 302 may include an additional column indicating whether the types of medical data may be shared.

The data access table 302 is indicated, in textual portion 304, as representing a "majority of patients" at a hospital (e.g., "Hospital A"). For example, a user of user interface 300 may have requested summary information related to its stored medical data. Thus, the user may view a snapshot of an average representation of data access rights determined from multitudes of executed agreements. Optionally, the user may specify a particular patient and view one or more data access tables associated with the specified patient. For example, the data access tables may vary according to context.

While the data access table 302 is illustrated as being a table, it may be appreciated that different graphical representations of the included information may be employed. For example, charts may be used.

Figure 3B:
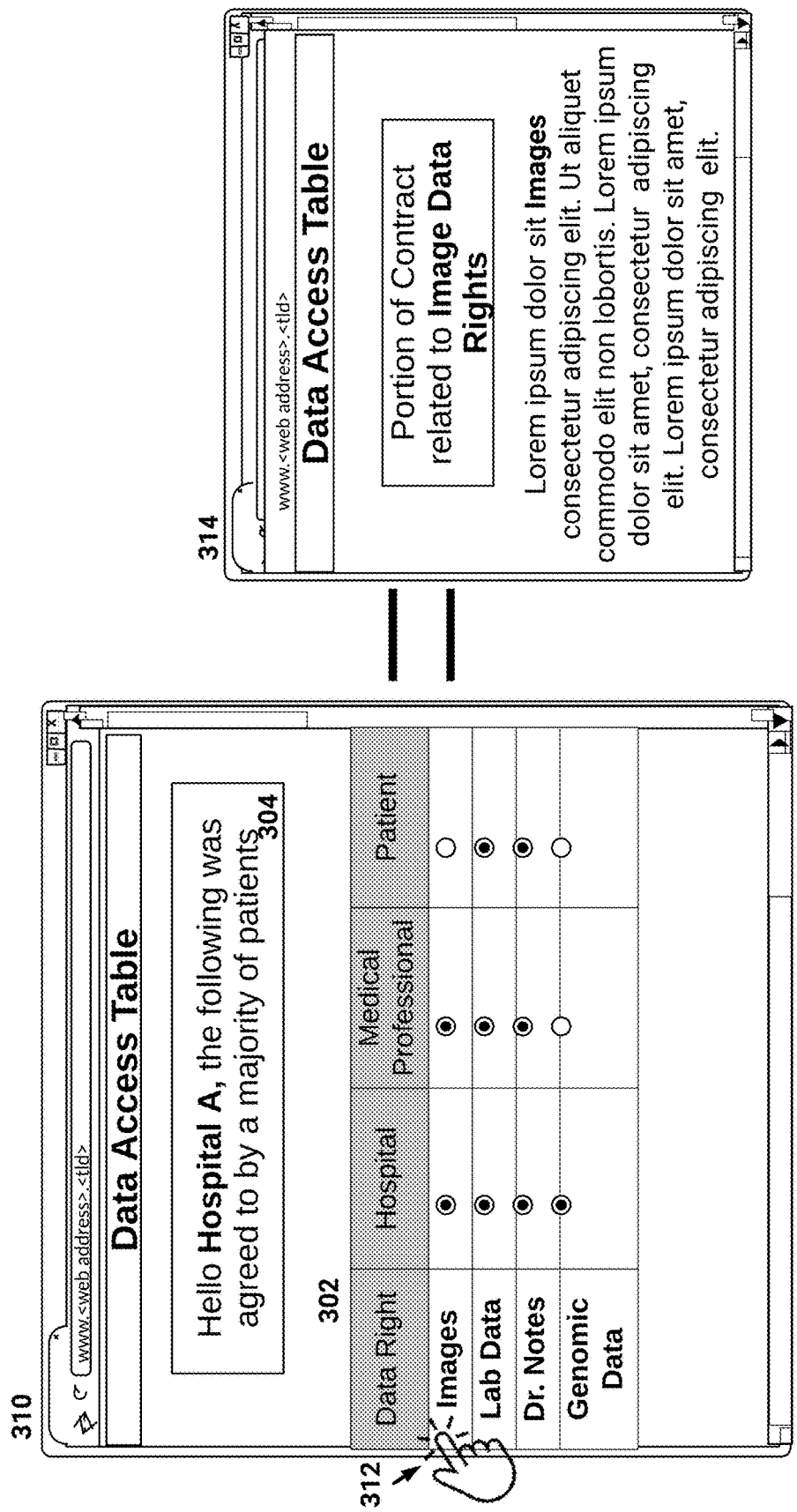
FIG. 3B illustrates an example user interface presenting a portion of an agreement related to a specific data access right.

FIG. 3B illustrates an example user interface 310 presenting a portion of an agreement related to a specific data access right 312. The illustrated data access table 302 may optionally respond to user input on a specific type of medical data (e.g., images). For example, a user may press on a touch-sensitive display for greater than a threshold amount of time. As another example, a user may press with greater than a threshold force or pressure. As another example, the user may provide voice commands. In response, the user interface 310 may update to present a portion of an agreement 314 that relates to the data access right 312. The portion presented may be obtained from a template used by the hospital (e.g., "Hospital A"). Optionally, the portion presented may represent language that is most commonly used in the hospital's agreements for that data access right 312. As illustrated, the user interface 314 may further identify (e.g., highlight or otherwise bold) a key-term identifying the type of medical data associated with the data access right 312. For example, the term "Images" is highlighted in the example user interface 314.

Figure 4:
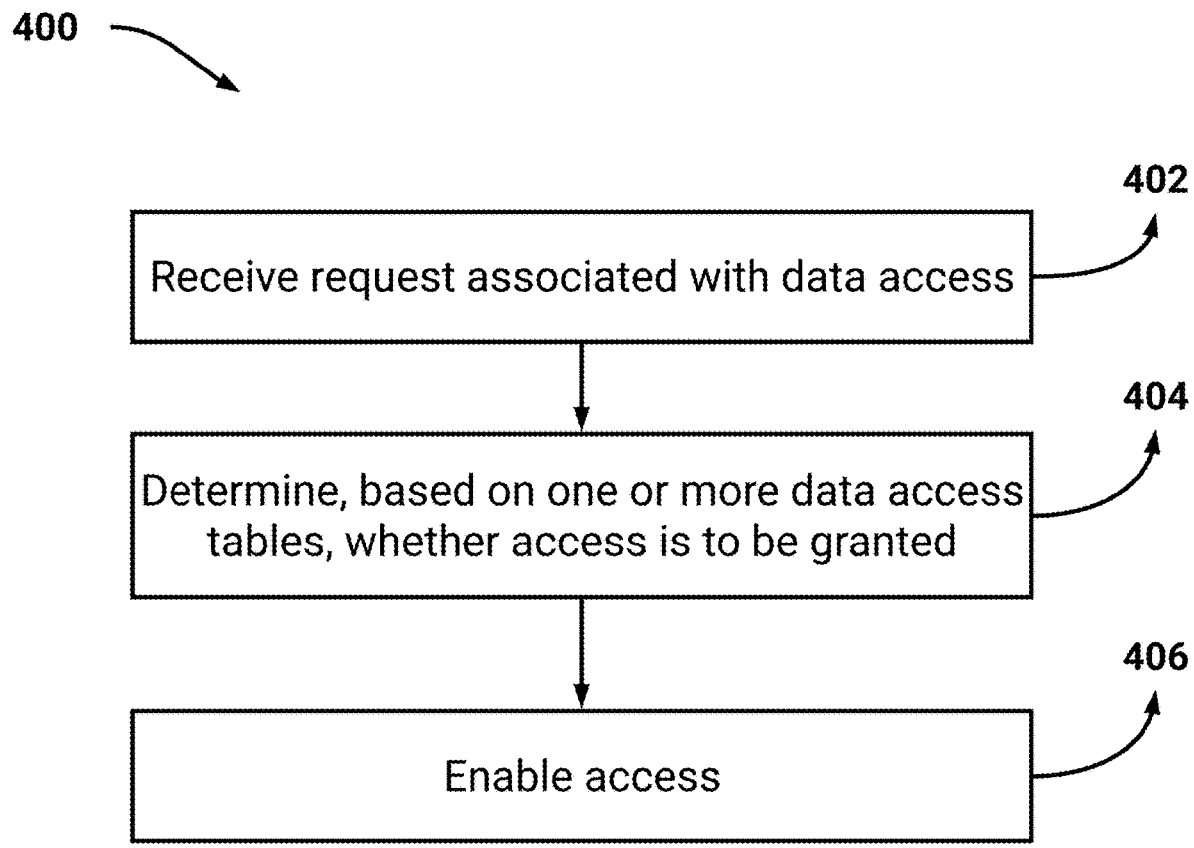
FIG. 4 is a flowchart of an example process for responding to requests for access to medical data.

FIG. 4 is a flowchart of an example process 400 for responding to requests for access to medical data. For convenience, the process 400 will be described as being performed by a system of one or more computers (e.g., the data rights ingestion and authorization system 100).

At block 402, the system receives a request associated with data access. As described in FIG. 1, the system may authorize requests for specific types of medical data. The request may thus indicate particular types of medical data being requested, such as the types illustrated in FIGS. 3A-3B. Optionally, the request may indicate a particular patient, or features associated with patients.

At block 404, the system determines whether access is to be granted. The system may access determined data access tables to identify whether access can be granted. Since the data access tables are generated based on analyzed agreements in place, the system may determine whether required entities have consented to the access. As an example, the request may indicate a request for medical information associated with a certain type of cancer. The system may analyze the data access tables to identify whether this medical information has been authorized for sharing by patients.

At block 406, the system enables access. The system may route the request to one or more storage systems or databases storing the requested data. Optionally, the system may route the request to one or more EMR systems which can identify medical data corresponding to the request. The system can then provide the requested medical information to the requesting entity. Optionally, the system may provide a reference to network locations storing the medical information. Optionally, the system may provide information identifying the requesting entity to an EMR system or other system associated with a hospital. The EMR system, as an example, may then create a network connection between itself and the requesting entity.

The medical data may thus be provided to the requesting entity. To ensure privacy, the medical data may be encrypted. For example, the medical data may be provided over HTTPS. As another example, the medical data may be encrypted according to a public key associated with the requesting entity. In this example, the system may provide the public key to the EMR system. Optionally, in implementations in which the system routes the medical data to the requesting entity, the system may encrypt the medical data.

In some embodiments, the system may provide medical data via a particular protocol. Additionally, the system and outside systems may communicate via the particular protocol. An example of the particular protocol may be the health communication protocol 120 described in U.S. Patent Pub. 2018/0211059, which is hereby incorporated by reference in its entirety.

Figure 5:
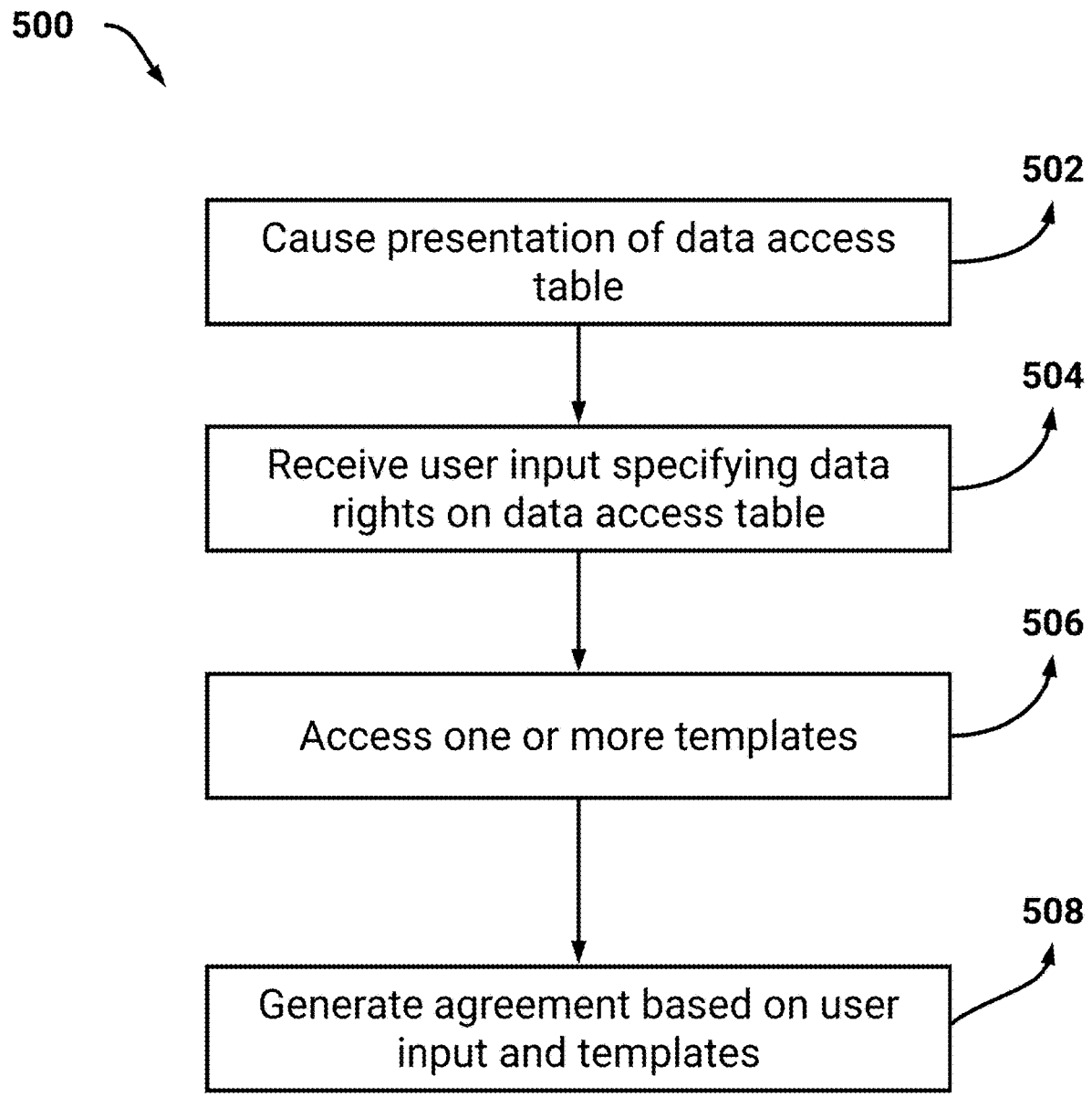
FIG. 5 is a flowchart of an example process for generating agreements based on a graphical depiction of a data access table.

FIG. 5 is a flowchart of an example process 500 for generating agreements based on a graphical depiction of a data access table. For convenience, the process 500 will be described as being performed by a system of one or more computers (e.g., the data rights ingestion and authorization system 100).

At block 502, the system causes presentation of a data access table in an interactive user interface. The interactive user interface may be, for example, similar to user interface 300 illustrated in FIG. 3A. However, the data access table may be presented without any toggling by entities for the medical data types.

At block 504, the system receives user input specifying data access rights on the presented data access table. For example, a user of the user interface may specify certain data access rights. The data access rights may be selected from among a template, or previously specified, set of data access rights. The user may additionally provide user input (e.g., textual input) indicating particular data access rights. The user may select specific entities to consent to data access rights for types of medical data. For example, the user may indicate that a hospital, medical professional, and patient consent to sharing medical notes. Optionally, the user may specify particular contexts. For example, the user may use a drop-down menu that presents available contexts. As another example, the user may textually describe a context. In this example, the system may analyze the text and identify a closest stored context.

At block 506, the system generates an agreement for execution. The system may analyze the data access rights specified in block 504, and determine the entities required to execute the agreement. For example, if only a hospital and patient are involved, then the system may generate an agreement that requires only their execution. To generate the agreement, the system can access templates associated with a particular hospital or medical care provider. These templates may indicate portions of agreements that relate to specific data access rights. Thus, the system can include the relevant portions.

The generated agreement may then be executed by any required entity. The system may optionally ingest this executed agreement, and then validate the agreement. Validation may include ensuring that the agreement is properly executed. Validation may also include analyzing the agreement to confirm it recites particular data access rights. Optionally, the required entities may execute the agreement via electronic schemes. For example, the system may present user interfaces associated with electronically signing agreements. These user interfaces may be presented on user devices of the entities, and they may execute the agreement based on authentication of the entities.

In this way, the system can increase efficiencies associated with generating agreements and ensuring data access rights are safeguarded. The system may therefore serve as a general front-end to data access rights.

Additional Implementation Details and Embodiments

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

As described above, in various embodiments certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computer system comprising one or more computer processors programed with software, which when executed causes the one or more computer processors to perform operations comprising:
   accessing a database of agreements, the agreements including indications of data access rights to portions of medical data;
   determining, based on the agreements, data access rights for a plurality of patients, the data access rights constraining access to portions of medical associated with the patients, and the data access rights requiring authorization of the patients and one or more entities; and
   generating an interactive user interface for presentation, wherein the interactive user interface:
      presents summary information data access rights for the patients, the summary information indicating average extents to which access to the portions of medical data are authorized for sharing; and
      responds to user input selecting at least one patient, and presents a data access table representing a graphical depiction of data access rights of the at least one patient.

2. The computer system of claim 1, wherein the interactive user interface is configured to respond to a query.

3. The computer system of claim 2, wherein the query indicates a context associated with sharing of medical data, and wherein the computer system determines a response based on the data access rights.

4. The computer system of claim 2, wherein the interactive user interface identifies portions to which a majority of the patients authorized sharing.

5. The computer system of claim 1, wherein the operations further comprise validating the plurality of agreements, and wherein validating comprises:
   obtaining one or more agreements between a first entity and a second entity, the agreements indicating particular data access rights to portions of medical data associated with first patients of the plurality of patients, such that the portions of medical data may be accessed by the first entity and the second entity; and
   identifying, based on generated data access tables for the first patients, whether the first patients authorized access to the portions of medical data.

6. The computer system of claim 5, wherein in response to an identification that one or more of the first patients did not authorize access, the operations further comprise:
   accessing a template associated with an agreement, the template including a textual portion associated with the particular data access rights; and
   generating, based on the accessed template, one or more agreements for execution by the one or more of the first patients.

7. The computer system of claim 1, wherein the summary information is specific to a context associated with use of medical data.

8. A method implemented by a system of one or more processors, the method comprising:
   accessing a database of agreements, the agreements including indications of data access rights to portions of medical data;
   determining, based on the agreements, data access rights for a plurality of patients, the data access rights constraining access to portions of medical associated with the patients, and the data access rights requiring authorization of the patients and one or more entities; and
   generating an interactive user interface for presentation, wherein the interactive user interface:
      presents summary information reflecting data access rights for the patients, the summary information indicating average extents to which access to the portions of medical data are authorized for sharing; and
      responds to user input selecting at least one patient, and presents a data access table representing a graphical depiction of data access rights of the at least one patient.

9. The method of claim 8, wherein the interactive user interface is configured to respond to a query.

10. The method of claim 9, wherein the query indicates a context associated with sharing of medical data, and wherein the computer system determines a response based on the data access rights.

11. The method of claim 9, wherein the interactive user interface identifies portions to which a majority of the patients authorized sharing.

12. The method of claim 8, wherein the operations further comprise validating the plurality of agreements, and wherein validating comprises:
   obtaining one or more agreements between a first entity and a second entity, the agreements indicating particular data access rights to portions of medical data associated with first patients of the plurality of patients, such that the portions of medical data may be accessed by the first entity and the second entity; and
   identifying, based on generated data access tables for the first patients, whether the first patients authorized access to the portions of medical data.

13. The method of claim 12, wherein in response to an identification that one or more of the first patients did not authorize access, the method further comprises:
   accessing a template associated with an agreement, the template including a textual portion associated with the particular data access rights; and generating, based on the accessed template, one or more agreements for execution by the one or more of the first patients.

14. The method of claim 8, wherein the summary information is specific to a context associated with use of medical data.

15. Non-transitory computer storage media storing instructions that when executed by a system of one or more computers, cause the one or more computers to perform operations comprising:
- accessing a database of agreements, the agreements including indications of data access rights to portions of medical data;
- determining, based on the agreements, data access rights for a plurality of patients, the data access rights constraining access to portions of medical associated with the patients, and the data access rights requiring authorization of the patients and one or more entities; and
- generating an interactive user interface for presentation, wherein the interactive user interface:
  - presents summary information reflecting data access rights for the patients, the summary information indicating average extents to which access to the portions of medical data are authorized for sharing; and
  - responds to user input selecting at least one patient, and presents a data access table representing a graphical depiction of data access rights of the at least one patient.

16. The computer storage media of claim 15, wherein the interactive user interface is configured to respond to a query.

17. The computer storage media of claim 16, wherein the query indicates a context associated with sharing of medical data, and wherein the computer system determines a response based on the data access rights.

18. The computer storage media of claim 16, wherein the interactive user interface identifies portions to which a majority of the patients authorized sharing.

19. The computer storage media of claim 15, wherein the operations further comprise validating the plurality of agreements, and wherein validating comprises:
- obtaining one or more agreements between a first entity and a second entity, the agreements indicating particular data access rights to portions of medical data associated with first patients of the plurality of patients, such that the portions of medical data may be accessed by the first entity and the second entity; and
- identifying, based on generated data access tables for the first patients, whether the first patients authorized access to the portions of medical data.

20. The computer system of claim 15, wherein the summary information is specific to a context associated with use of medical data.

* * * * *